US006170980B1

(12) United States Patent
Martin

(10) Patent No.: US 6,170,980 B1
(45) Date of Patent: Jan. 9, 2001

(54) AUTOMATED TABLET DISSOLUTION APPARATUS

(75) Inventor: Arthur L. Martin, Holliston, MA (US)

(73) Assignee: Source for Automation, Inc., Holliston, MA (US)

( * ) Notice: Under 35 U.S.C. 154(b), the term of this patent shall be extended for 0 days.

(21) Appl. No.: 09/395,852

(22) Filed: Sep. 14, 1999

Related U.S. Application Data

(60) Provisional application No. 60/128,625, filed on Apr. 9, 1999.

(51) Int. Cl.[7] ................................. G01N 1/38; B01F 1/00
(52) U.S. Cl. ..................... 366/191; 366/194; 366/144; 366/226; 366/241; 422/270; 422/283; 73/866
(58) Field of Search .................................. 366/184, 190, 366/191, 194, 195, 279, 226, 144, 241; 422/99, 100, 225, 940, 232, 269, 270, 287, 261, 283, 285; 73/866

(56) References Cited

U.S. PATENT DOCUMENTS

| 3,860,394 | * | 1/1975 | Tepas, Jr. et al. . |
| 4,464,340 | * | 8/1984 | Lennox, Jr. et al. . |
| 4,578,244 | * | 3/1986 | Cosgrove, Jr. et al. . |
| 4,792,434 | | 12/1988 | Metzger et al. . |
| 4,856,909 | | 8/1989 | Mehta et al. . |
| 4,879,917 | * | 11/1989 | Eppelmann et al. . |

(List continued on next page.)

OTHER PUBLICATIONS

Article entitled, "A fully automated, benchtop dissolution testing workstation," by Richard Buechsenschuetz, published before present application.
Sales literature for Zymark Corp.'s Multidose workstation, published before present application.
Sales literature for Scientific Instruments and Technology Corp.'s Pharma Test dissolution baths, published before present application.

* cited by examiner

Primary Examiner—Tony G. Soohoo
(74) Attorney, Agent, or Firm—Kriegsman & Kriegsman

(57) ABSTRACT

An automated tablet dissolution apparatus adapted for use with tablet sinkers. In a preferred embodiment, the apparatus includes a dissolution vessel and an automated mechanism for agitating the contents of the dissolution vessel. The apparatus also includes an automated mechanism for measuring a desired volume of media, heating and degassing the volume and then dispensing the volume into the vessel, an automated mechanism for sampling the contents of the dissolution vessel, an automated mechanism for dispensing a tablet (and sinker, if desired) into the dissolution vessel, an automated mechanism for heating the dissolution vessel, and an automated mechanism for imaging the contents of the dissolution vessel. In addition, the apparatus includes an automated mechanism for emptying the contents of the dissolution vessel. According to one embodiment, such a vessel emptying mechanism includes (a) a waste media receptacle, the waste media receptacle having an inlet opening and defining a media chamber, (b) a first tube, the first tube having a first end and a second end, the first end being insertable into the dissolution vessel, (c) a second tube, the second tube having a first end and a second end, the first end of the second tube being connected to the second end of the first tube, (d) a sinker strainer disposed between the dissolution vessel and the waste media receptacle for straining a sinker from the fluid contents of a dissolution vessel, the sinker strainer having an inlet opening and an outlet opening, the second end of the second tube being connected to the inlet opening of the sinker strainer, (e) a third tube, the third tube having a first end and a second end, the first end of the third tube being connected to the outlet opening of the strainer, the second end of the third tube being connected to the inlet opening of the waste media receptacle, and an automated vacuum mechanism for drawing the contents of the dissolution vessel up through the first end of the first tube towards the media chamber of the waste media receptacle.

14 Claims, 11 Drawing Sheets

U.S. PATENT DOCUMENTS

| | | |
|---|---|---|
| 4,924,716 | 5/1990 | Schneider . |
| 5,639,974 * | 6/1997 | Hanson et al. . |
| 5,682,001 * | 10/1997 | Hanson et al. . |
| 5,816,701 | 10/1998 | Martin et al. . |
| 6,006,777 * | 12/1999 | Renslow . |

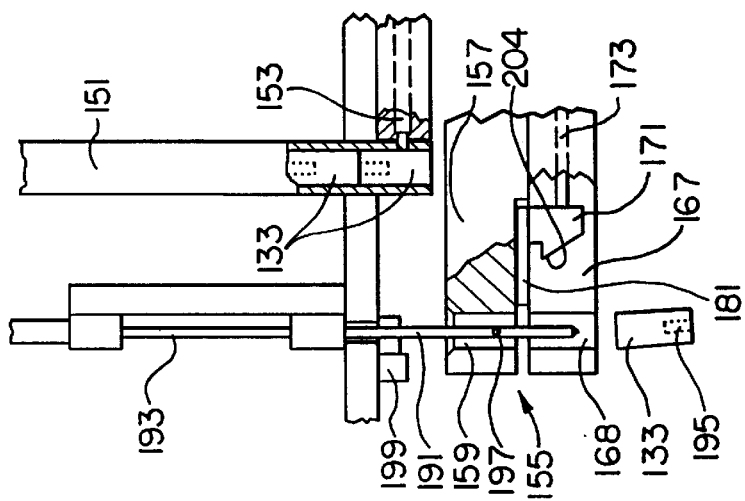
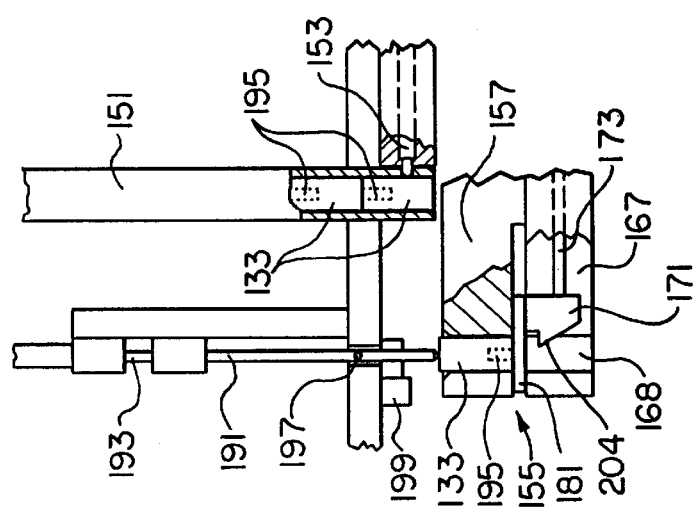
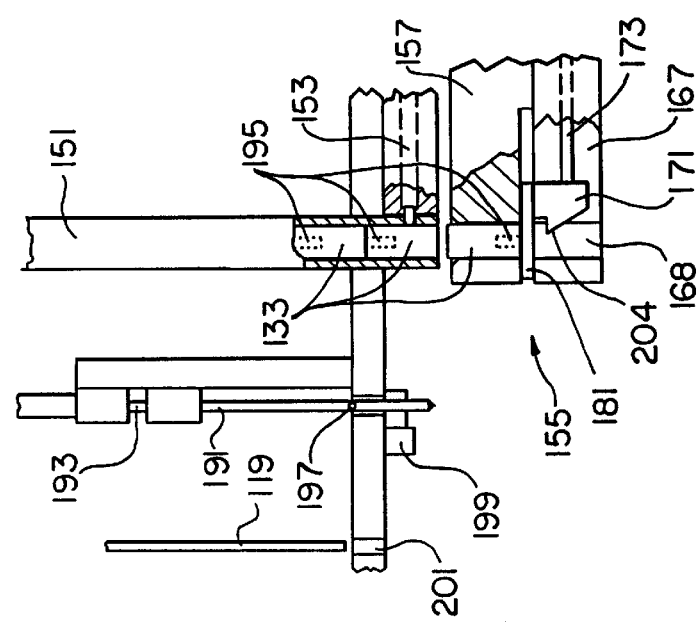

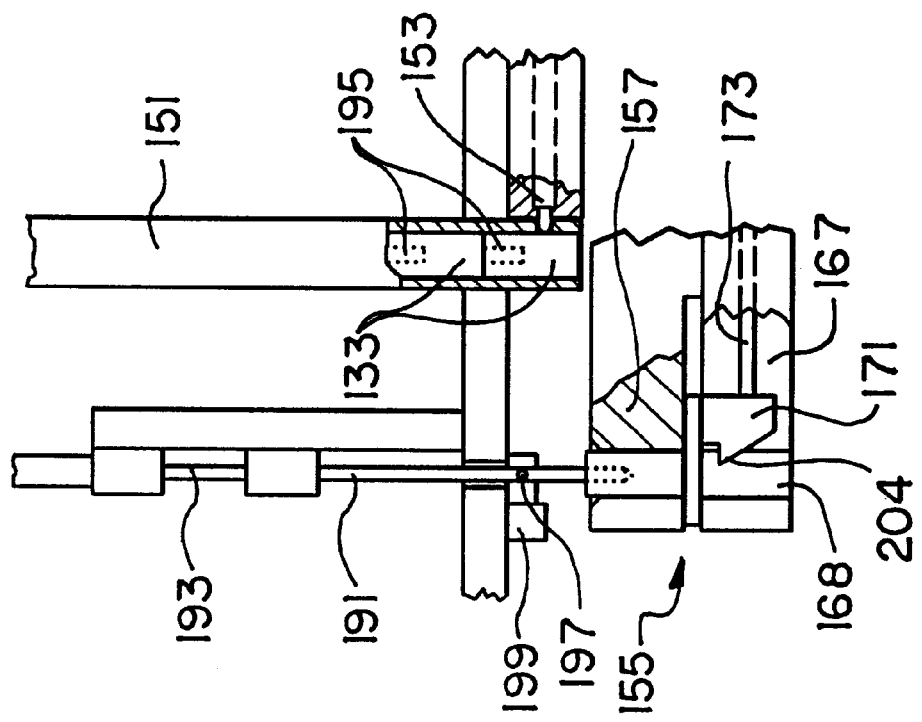
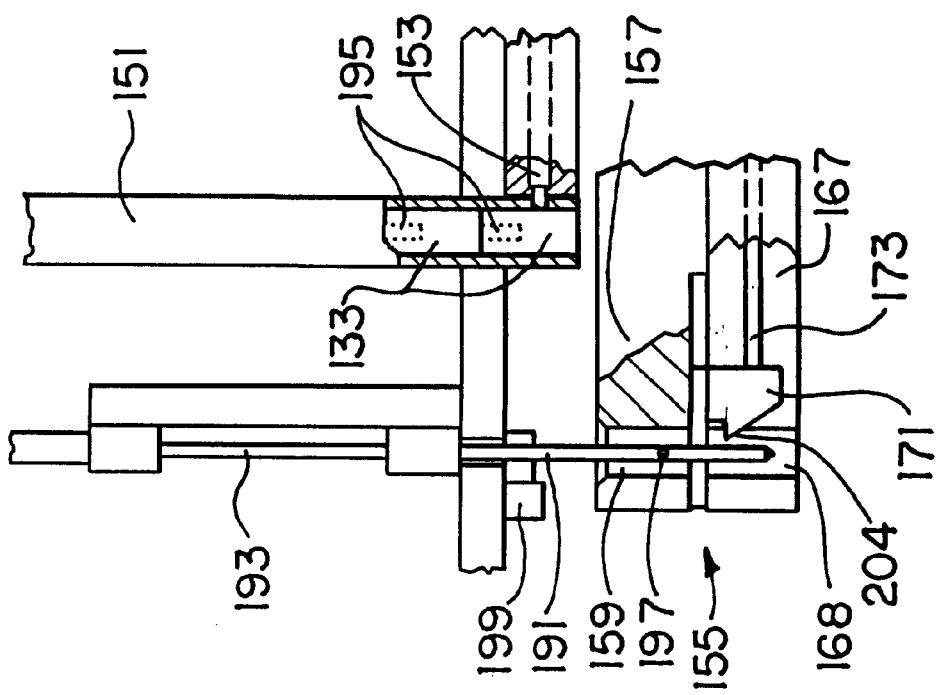
FIG. 16(c)
FIG. 16(e)

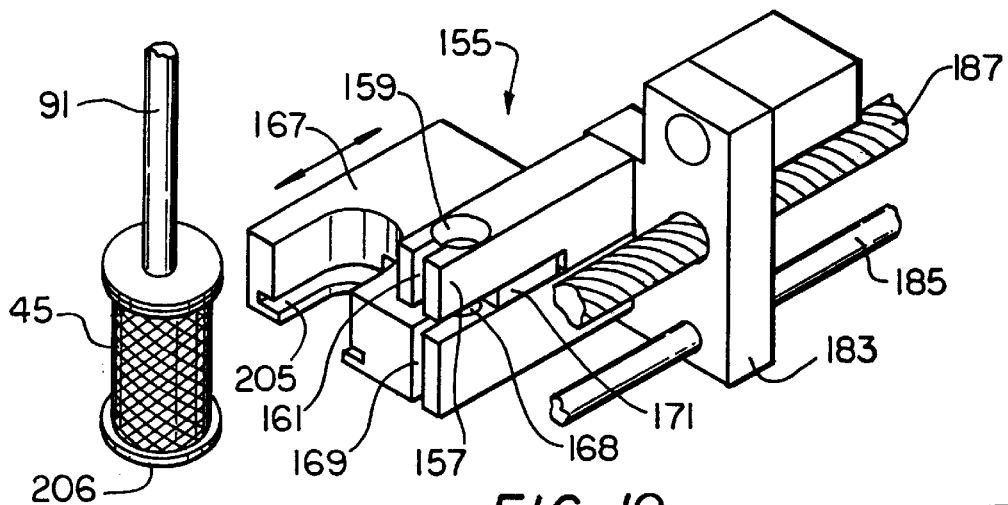
FIG. 19
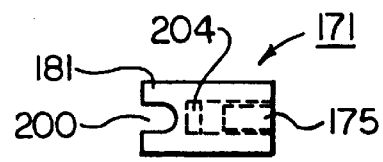
FIG. 18(a)
FIG. 17(b)
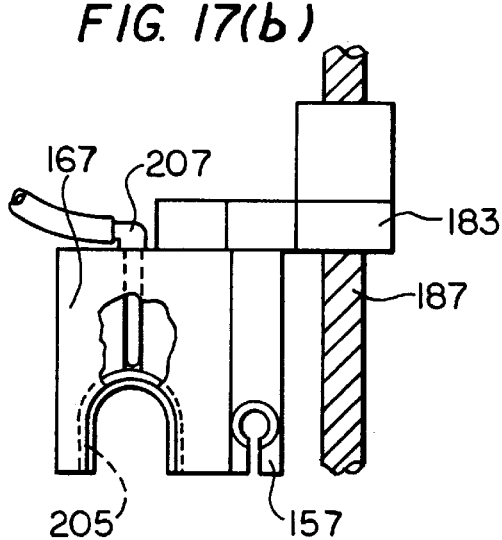
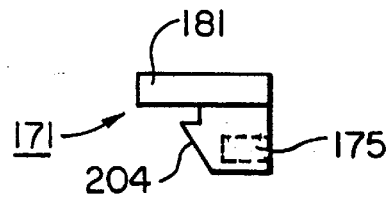
FIG. 18(b)
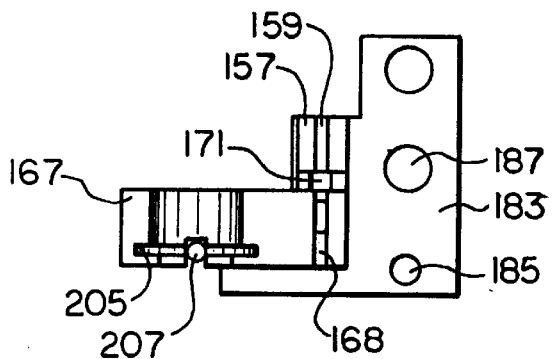
FIG. 17(a)

AUTOMATED TABLET DISSOLUTION APPARATUS

CROSS-REFERENCE TO RELATED APPLICATIONS

This application claims the benefit under 35 U.S.C. § 119(e) of U.S. Provisional Patent Application Ser. No. 60/128,625, filed Apr. 9, 1999, the disclosure of which is incorporated herein by reference.

BACKGROUND OF THE INVENTION

The present invention relates generally to tablet dissolution testing and more particularly to a novel tablet dissolution apparatus.

In the pharmaceutical industry, it is commonplace, during pharmaceutical formulation development, stability determination, analytical development, quality control, or otherwise, to ascertain the rate at which a drug in solid form (hereinafter referred to as a "tablet") dissolves under certain well-defined conditions. In this manner, one can gauge or predict the dissolution rate of the tablet in the human stomach. Historically, tablet dissolution testing has been performed largely manually; however, recently, certain automated tablet dissolution apparatuses have been developed.

For example, in commonly-assigned U.S. Pat. No. 5,816,701, inventors Martin et al., which issued Oct. 6, 1998, and which is herein incorporated by reference, there is disclosed one such automated tablet dissolution apparatus. In a preferred embodiment, the apparatus of the aforementioned patent includes a dissolution vessel removably seated within an aluminum platen. The apparatus also includes an assembly for automatically measuring a desired volume of media, heating and degassing the volume of media and then dispensing the volume of media into the dissolution vessel. In addition, the apparatus includes a carousel having a plurality of compartments, the carousel being rotatably mounted on a stage, the stage being alignable with the vessel. According to one mode of operation, an open-top, cage-type basket is placed in one or more compartments of the carousel, each basket containing a tablet intended for dissolution. The apparatus additionally includes a shaft aligned with the vessel, the bottom end of the shaft being adapted to frictionally fit together with a basket. The shaft is rotatable and vertically movable so that it can fit together with a basket, pick the basket up out of the carousel, lower the basket into the vessel, rotate the basket within the media and remove the basket from the media. The apparatus further includes a catheter automatically movable in and out of the vessel for sampling the media at desired times, an automated mechanism for loading and replacing a depth filter on the input end of the catheter, an automated mechanism for removing the basket from the end of the shaft after testing has been completed and an automated mechanism for removing media from the vessel after testing has been completed. The apparatus also includes a paddle shaft which may be used interchangeably with the basket shaft if tablets are placed directly in the compartments of the carousel and are then dispensed from the carousel into the vessel through an opening in the bottom of each carousel that is alignable with an opening in the stage.

Although the aforementioned automated tablet dissolution apparatus works well with tablets whose dissolution is typically effected using a rotatably-driven, cage-type basket and also works well with tablets that do not float on top of the media and whose dissolution is typically effected using a rotatably-driven paddle, the above-described automated apparatus cannot be used to test tablets that float on top of the media and whose dissolution is typically effected by placing such a tablet in a weighted "sinker" and then using a rotatably-driven paddle to cause the dissolution of the tablet in the sinker. One reason why the above-described automated tablet dissolution apparatus cannot be used with tablets requiring the use of sinkers is that said apparatus is not designed for the automated retrieval of a sinker from the dissolution vessel following the testing period.

Typically, when sinkers are used with conventional non-automated testing equipment, they are retrieved manually. The present inventor is aware of one automated tablet dissolution apparatus in which a specially-designed sinker is retrieved with a robotic assembly. However, as can readily be appreciated, the aforementioned automated tablet dissolution apparatus comprising the foregoing robotic assembly is limited in its usefulness to testing those tablets for which use of the specially-designed sinker is accepted. Consequently, because certain tablets have dissolution protocols that require the use of specific sinkers, the foregoing robotic system does not have broad applicability.

SUMMARY OF THE INVENTION

It is an object of the present invention to provide a novel tablet dissolution apparatus.

It is another object of the present invention to provide a novel tablet dissolution apparatus that overcomes at least some of the shortcomings of the apparatuses described above.

It is still another object of the present invention to provide a tablet dissolution apparatus that is adapted for use with a variety of sinkers (although not limited to use therewith) and that can be used to automatically remove a sinker from a dissolution vessel (if one is present therein) following testing.

According to one aspect or feature of the invention, there is provided a tablet dissolution apparatus, said tablet dissolution apparatus including a dissolution vessel and a novel automated mechanism for emptying the contents of said dissolution vessel, said automated emptying mechanism preferably comprising (a) a waste media receptacle, said waste media receptacle having an inlet opening and defining a media chamber; (b) tubing means having a first end insertable into the dissolution vessel and a second end attached to said inlet opening of said waste media receptacle; (c) automated means for moving said first end of said tubing means into and out of, respectively, the dissolution vessel; (d) automated vacuum means for creating a vacuum drawing from within said waste media receptacle to said first end of said tubing means, said vacuum being sufficiently strong to empty the contents of said dissolution vessel; and (e) a sinker strainer disposed between said first end of said tubing means and said media chamber.

According to a first embodiment, said sinker strainer is disposed in-line between said waste media receptacle and said first end of said tubing means.

According to a second embodiment, said sinker strainer is disposed within said waste media receptacle.

BRIEF DESCRIPTION OF THE DRAWINGS

The accompanying drawings, which are hereby incorporated into and constitute a part of this specification, illustrate a preferred embodiment of the invention and, together with the description, serve to explain the principles of the invention. In the drawings wherein like reference numerals represent like parts:

FIGS. 16(a) through 16(e) are fragmentary side elevation views, partly in section and broken away in part, illustrating the operation of the depth filter feeding and ejecting mechanism of the apparatus of FIG. 1;

FIGS. 17(a) and 17(b) are front and top views, respectively, of the carriage assembly of the depth filter feeding and ejecting mechanism of FIGS. 16(a) through 16(e);

FIGS. 18(a) and 18(b) are top and side elevation views, respectively, of the plunger shown in FIGS. 16(a) through 16(e);

FIG. 19 is a perspective view illustrating how the carriage assembly of the depth filter feeding and ejecting mechanism can also be used to detach a basket from the basket shaft.

DETAILED DESCRIPTION OF PREFERRED EMBODIMENTS

Figure 1:
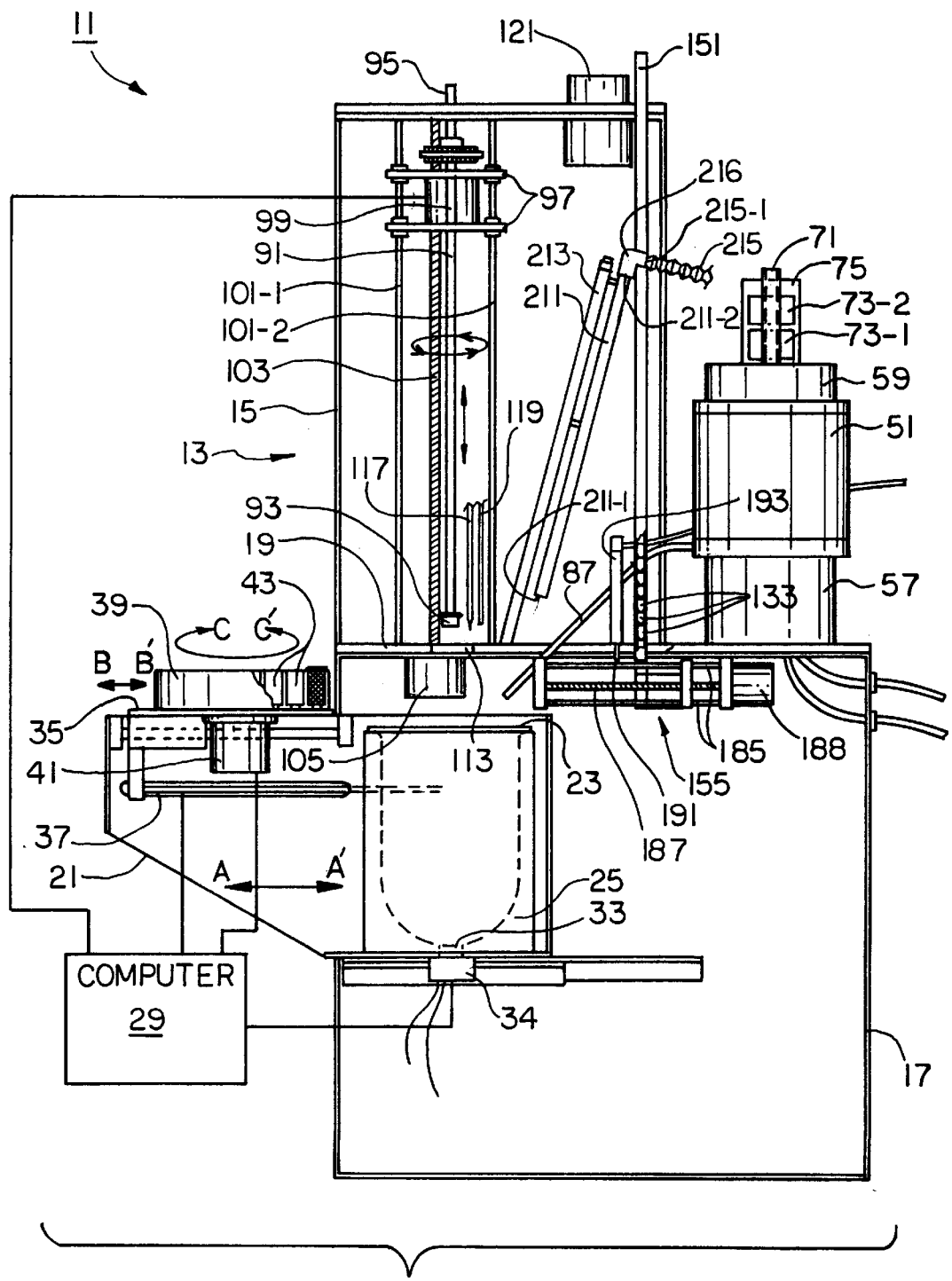
FIG. 1 is a simplified, partly schematic, fragmentary, side elevation view, broken away in part, of a first embodiment of an automated tablet dissolution apparatus constructed according to the teachings of the present invention, certain aspects of the automated tablet dissolution apparatus not being shown to improve clarity.
Figure 2:
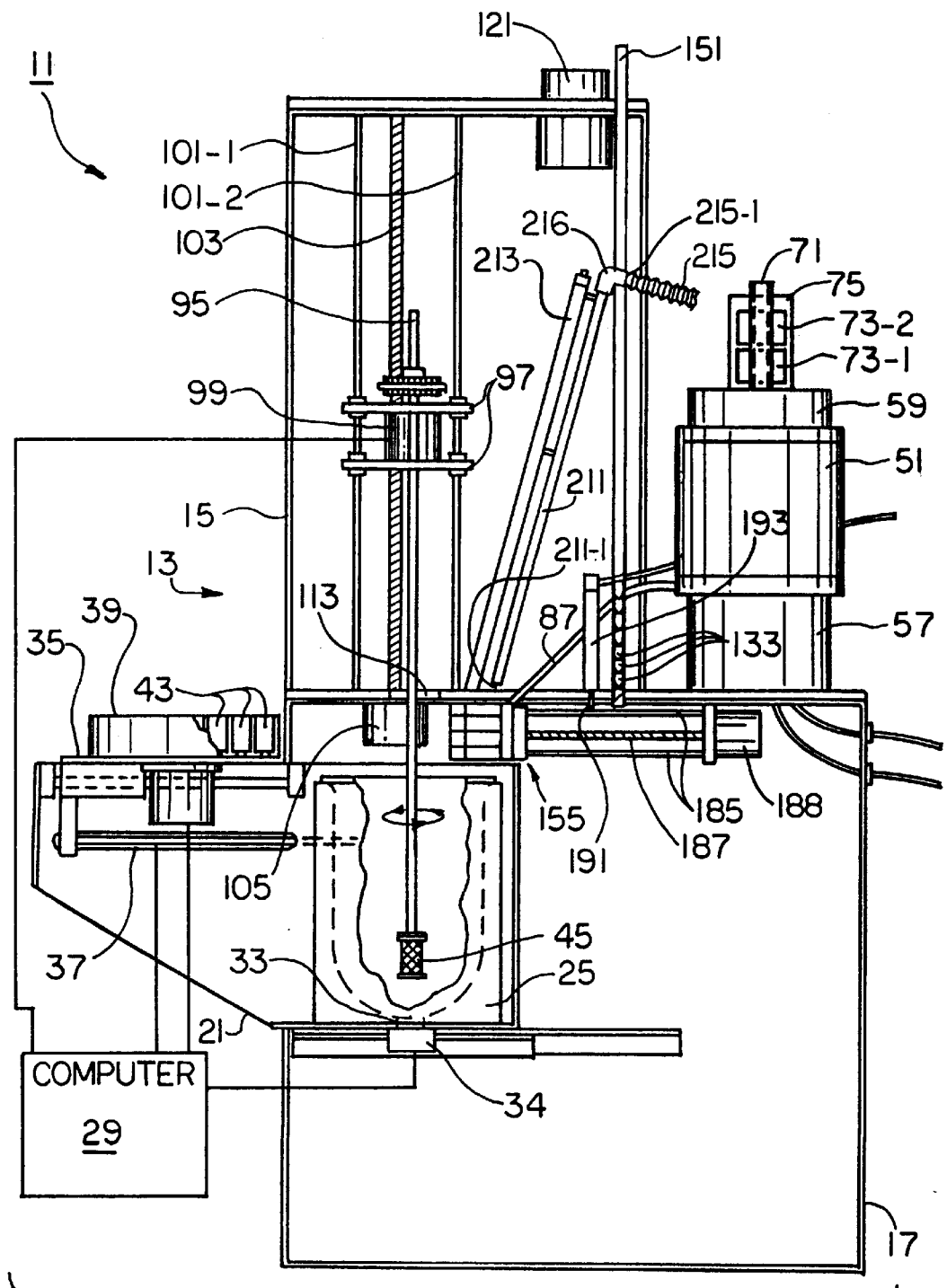
FIG. 2 is a simplified, partly schematic, fragmentary, side elevation view, broken away in part, of the automated tablet dissolution apparatus of FIG. 1, depicting the automated tablet dissolution apparatus during the tablet dissolution stage of its operation, certain aspects of the automated tablet dissolution apparatus not being shown to improve clarity.
Figure 3:
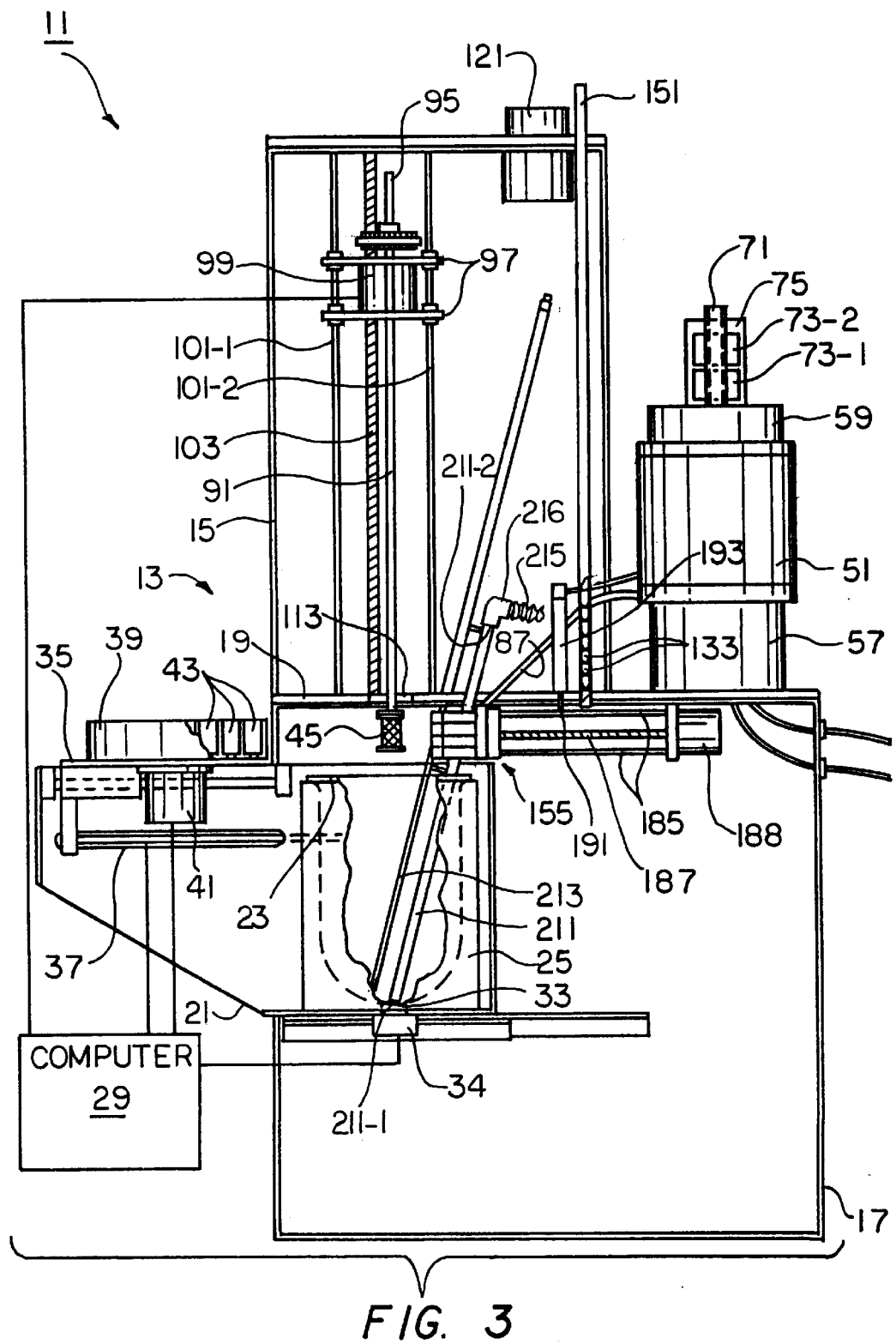
FIG. 3 is a simplified, partly schematic, fragmentary, side elevation view, broken away in part, of the automated tablet dissolution apparatus of FIG. 1, depicting the automated tablet dissolution apparatus during the vessel emptying stage of its operation, certain aspects of the automated tablet dissolution apparatus not being shown to improve clarity.

Referring now to FIGS. 1 through 5, there are shown various views of one embodiment of an automated tablet dissolution apparatus constructed according to the teachings of the present invention, the automated tablet dissolution apparatus being represented generally by reference numeral 11. Those aspects of apparatus 11 not pertinent to the present invention are neither shown in the drawings nor described herein for clarity.

Apparatus 11 includes a housing 13, which may be made of metal or a similarly suitable structurally-durable material. Housing 13 includes an upper portion 15 and a lower portion 17, upper portion 15 and lower portion 17 being separated by a platform 19. A drawer 21 is mounted within lower portion 17 of housing 13, drawer 21 being manually slidable forwards and backwards within lower portion 17 in the directions indicated by arrows A and A', respectively, for reasons hereinafter to become apparent.

Figure 8:
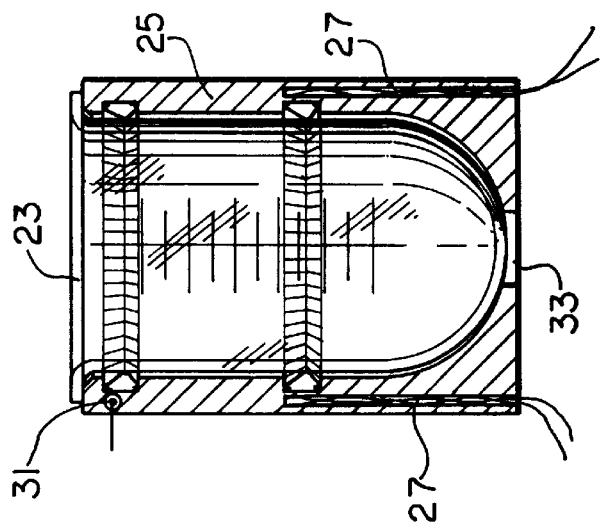
FIG. 8 is a view, partly in section, of the dissolution vessel of FIG. 6 removably seated within the platen of the heating assembly of FIG. 7.
Figure 7:
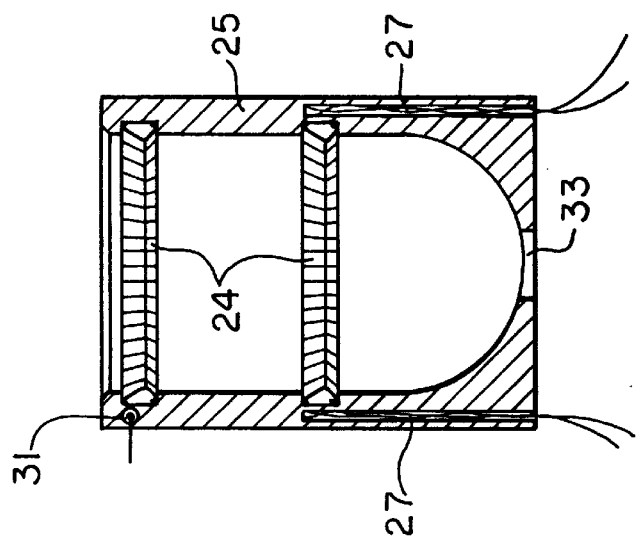
FIG. 7 is a partly schematic section view of the dissolution vessel heating assembly for the apparatus of FIG. 1.
Figure 6:
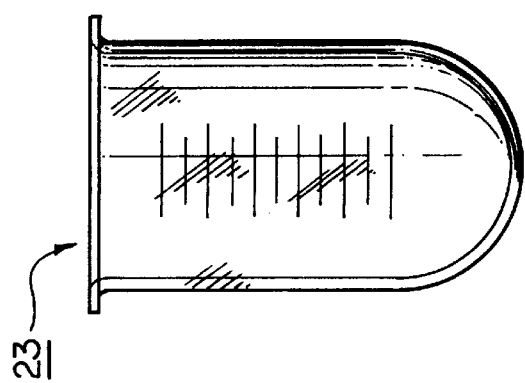
FIG. 6 is an enlarged front elevation view of the dissolution vessel of the automated tablet dissolution apparatus of FIG. 1.
Figure 10:
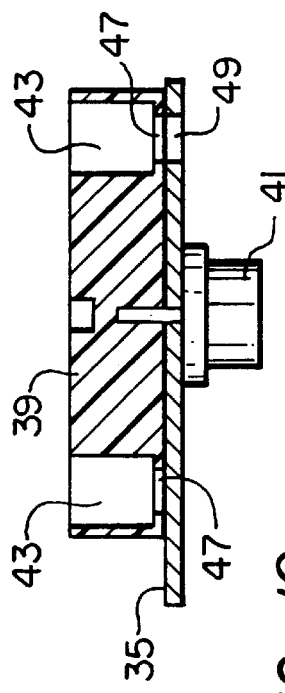
FIG. 10 is a section view of the assembly of FIG. 9, with one of the compartments of the carousel being shown aligned with the tablet opening in the stage.
Figure 11:
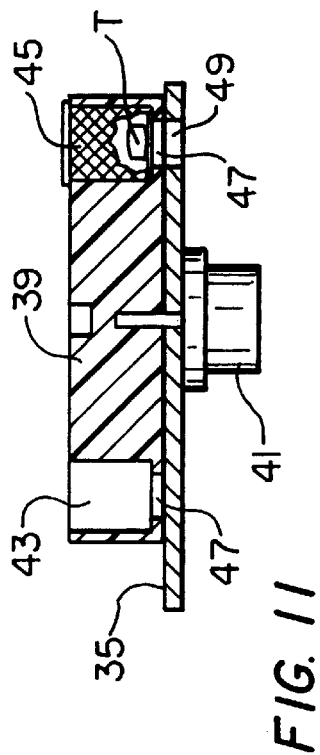
FIG. 11 is a section view, broken away in part, of the assembly of FIG. 9, a tablet-containing basket being shown loaded into one of the compartments of the carousel.

Apparatus 11 also includes a dissolution vessel 23 (seen best in FIG. 6). In the present embodiment, vessel 23 is a 1 liter transparent glass vessel of the type conventionally used in tablet dissolution apparatuses. Apparatus 11 additionally includes means for heating the contents of dissolution vessel 23. Referring now to FIGS. 7 and 8, in the present embodiment, said means for heating the contents of dissolution vessel 23 can be seen to include a metal platen 25. Platen 25, which is preferably made of aluminum or a similarly suitable heat-conductive material, is appropriately sized and shaped to removably receive vessel 23. A plurality of heat-conductive fingers 24 used to promote heat transfer from platen 25 to vessel 23 are affixed to the interior surface of platen 25 and are adapted for contact with vessel 23 when vessel 23 is seated within platen 25. A plurality of resistive heating elements 27 are disposed within platen 25 to heat platen 25. The outputs of elements 27 are controlled by a computer 29 (see FIG. 1). (For convenience and clarity, certain connections between computer 29 and other components of apparatus 11 are not shown.) A thermistor 31, which is also connected to computer 29, is also disposed within platen 25 to determine the temperature of platen 25. In this manner, using suitable calibration curves, computer 29 can be used to control the temperature at which the contents of vessel 23 are maintained by monitoring the temperature of platen 25 with thermistor 31 and accordingly adjusting the outputs of heating elements 27. Typically, the contents of vessel 23 are maintained at a temperature of 37° C.

Referring back now to FIGS. 1 through 3, vessel 23 and platen 25 can be seen to be positioned within the rear of drawer 21. Vessel 23 can be removed from apparatus 11 (e.g., for washing or replacement) by pulling drawer 21 forwardly in the direction of arrow A and lifting vessel 23 out of platen 25. Alternatively, in another embodiment (not shown), instead of being provided with a slidably mounted drawer 21, housing 13 may be provided with a hingedly mounted full-length front door that swings open to expose platen 25, platen 25 being pivotally mounted on a plate within housing 13 so that it may be tipped forwardly in order to facilitate removal of vessel 23 therefrom. A catch basin in which platen 25 may be seated may be used to catch any inadvertent overflow of media thereover.

An opening 33 is provided in the bottom of platen 25. A camera 34, which is controlled by and whose output is fed to computer 29, is aligned with opening 33 so that one or more images, as desired, may be taken of the contents of vessel 23. Such images may be stored in computer 29 (and, if desired, printed out by a printer (not shown) connected to computer 29) and may be used, for example, to verify that a tablet was dropped correctly into vessel 23 and/or that the tablet was dissolved properly. Although not shown, one or more openings like opening 33 may be provided in the side wall of platen 25 to permit an additional camera to be deployed from a different vantage point than that of camera 34 or to permit an individual to visually inspect the contents of vessel 23. Alternatively, in another embodiment (not shown), instead of using camera 34 and one or more fixed cameras on the side of vessel 23, a single camera pivotally mounted on a stand fixed next to the platen may be used. In this manner, by tilting the camera, a variety of views of the side and bottom of vessel 23 can be obtained.

Apparatus 11 further comprises a stage 35 disposed within drawer 21. Stage 35 is mechanically coupled to an air cylinder 37. Air cylinder 37, which is controlled by computer 29, moves stage 35 forwards and backwards within drawer 21 in the directions indicated by arrows B and B', respectively. A carousel 39 is rotatably mounted on top of stage 35. Rotation of carousel 39 in the directions indicated by arrows C and C' is caused by a motor 41, which is controlled by computer 29. Alternatively, where housing 13 is not provided with a drawer 21, but rather, is provided with a full-length, hingedly-mounted front door (not shown), stage 35 may be replaced with a support rail pivotally attached to housing 13, carousel 39 being rotatably mounted on the support rail and being made to pivot in and out of position over vessel 23 by air cylinder 37. Rotation of carousel 39 on the support rail may be achieved using a belt coupled to motor 41.

Figure 12:
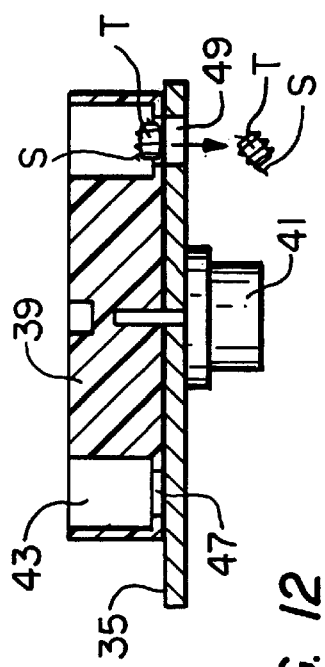
FIG. 12 is a section view of the assembly of FIG. 9, a tablet being shown loaded into one of the compartments of the carousel to illustrate how a tablet may be dispensed from the carousel through the tablet opening in the stage.
Figure 9:
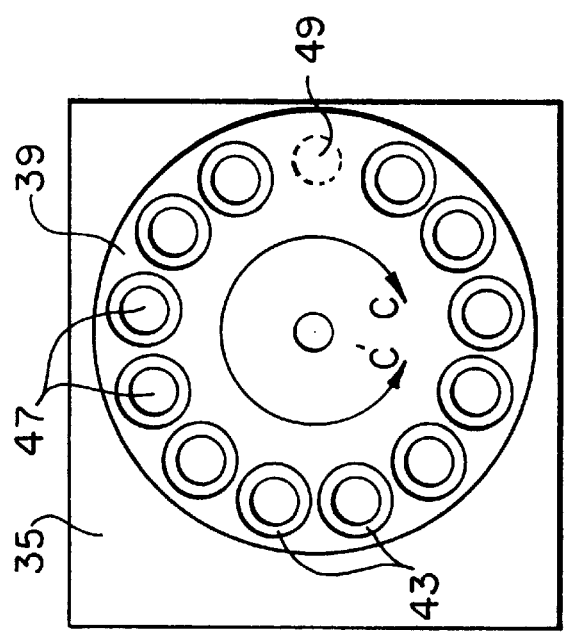
FIG. 9 is a plan view of the stage, carousel and carousel motor shown in FIG. 1.

Referring now to FIGS. 9 through 12, additional details of stage 35 and carousel 39 are shown. As can be seen, carousel 39 is shaped to include a plurality of compartments 43. Each compartment 43 is appropriately dimensioned to removably receive a cage-type, open-top basket 45 (see FIG. 11) adapted to hold a tablet T (to enable apparatus 11 to be used for basket-type dissolution). In addition, the bottom of each compartment 43 is provided with an opening 47 sufficiently large to permit a tablet T (where tablet T is of the type that, on its own, will sink into the dissolution media) or, as seen in FIG. 12, the combination of a tablet T and a sinker S (where tablet T is of the type that, without a sinker S, will float to the top of the dissolution media) to pass therethrough but small enough to prevent basket 45 from passing therethrough. An opening 49 appropriately dimensioned to permit tablet T or the combination of tablet T and sinker S to pass therethrough is also provided in stage 35. Preferably, openings 47 and 49 are large enough to accommodate a variety of different types of sinkers. Opening 49, which is aligned with vessel 23 when stage 35 is in its rearwardmost position within drawer 21, may be aligned with opening 47 of each compartment 43 by rotating carousel 39. In this manner, as can be seen in FIG. 12, when a basket-less compartment 43 containing a tablet T or the combination of a tablet T and a sinker S is aligned with opening 49, the tablet T or tablet T and sinker S can drop through openings 47 and 49 (and into vessel 23) to enable apparatus 11 to be used for paddle-type dissolution.

Figure 14:
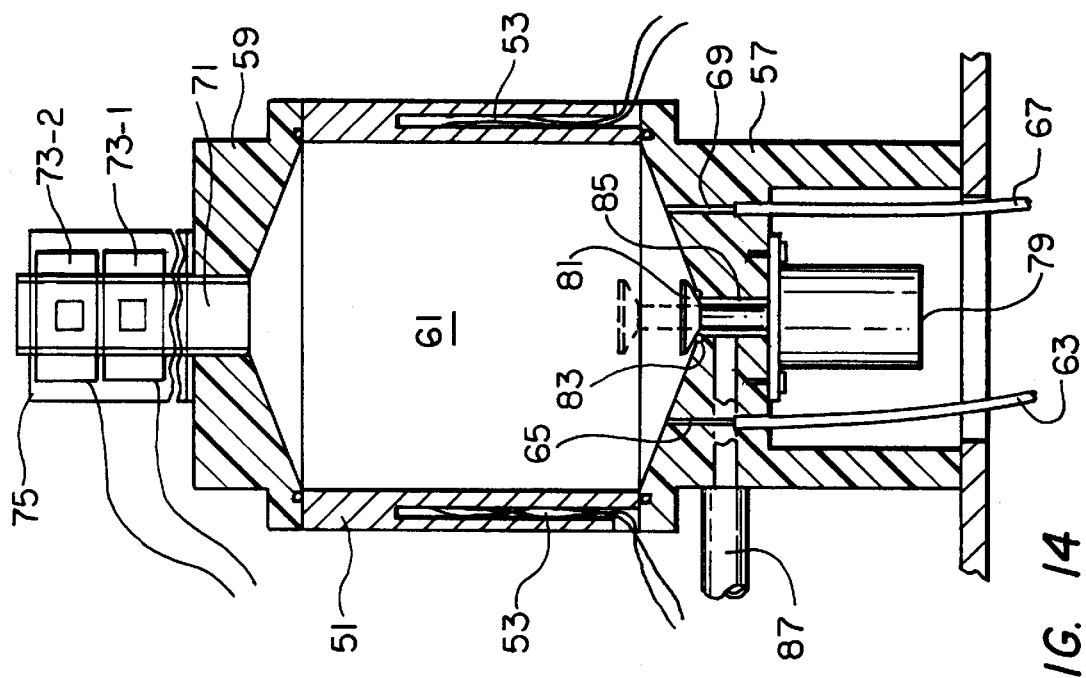
FIG. 14 is a section view of the preheating, sparging and dispensing assembly shown in FIG. 13.
Figure 13:
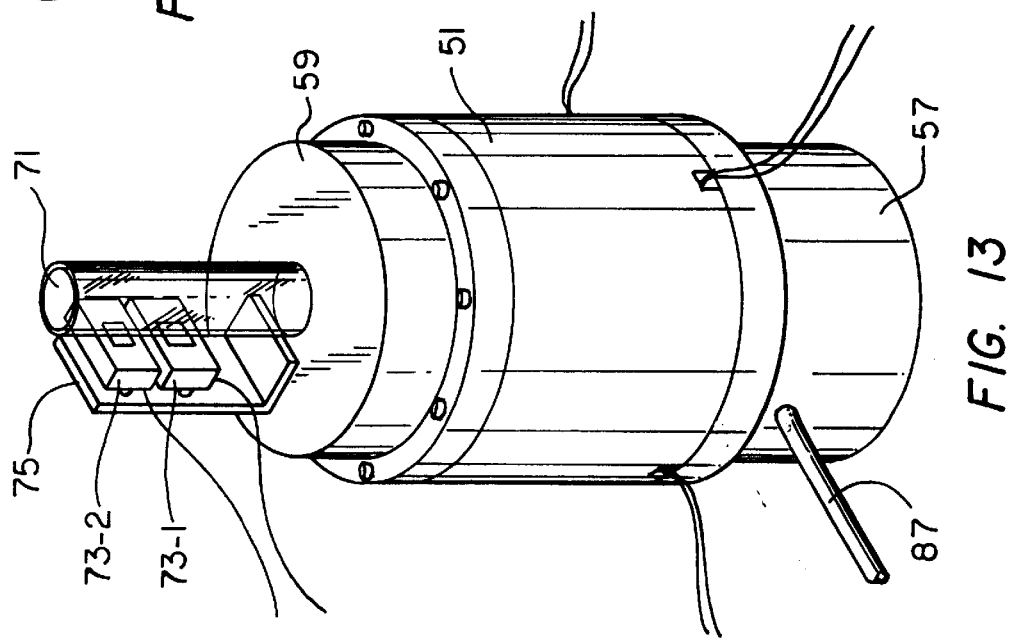
FIG. 13 is an enlarged perspective view of the assembly shown in FIG. 1 for preheating, sparging and dispensing a volumetrically determined quantity of media into the dissolution vessel.

Referring back now to FIGS. 1 through 3, apparatus 11 further comprises means for dispensing a volumetrically-measured quantity of pre-heated, sparged (i.e., de-gassed) media into vessel 23. As can best be seen in FIGS. 13 and 14, said dispensing means comprises, in the present embodiment, a cylindrical platen 51, which is preferably made of aluminum coated with TEFLON (synthetic resin polymer) or a similarly suitable heat-conductive, non-stick surface. A plurality of resistive heating elements 53, connected to and controlled by computer 29, are disposed within platen 51. Platen 51 is mounted on top of a base member 57, and a cover 59 is mounted on top of platen 51. Platen 51, base member 57 and cover 59 jointly define a media chamber 61. Media is introduced into chamber 61 from an external source (not shown) through tubing 63 inserted into a media input channel 65 formed in base member 57. Once in chamber 61, the media is pre-heated via platen 51 to a temperature slightly higher than that desired for dissolution (e.g., about 38° C.) so that, during transport from chamber 61 to vessel 23, the media may cool to the appropriate dissolution temperature. Helium, which is added to the media in order to sparge (i.e., de-gas) the media, is introduced into chamber 61 from an external source (not shown) through tubing 67 inserted into a helium input channel 69 formed in base member 57.

A section of clear tubing 71 is mounted within cover 59 so that one end thereof is placed in fluid communication with chamber 61 and so that the other end thereof extends upwardly a short distance beyond the top of cover 59. A pair of media detectors 73-1 and 73-2, which are connected to computer 29, are mounted on a bracket 75 extending parallel to tubing 71. Detector 73-1 is appropriately vertically positioned on bracket 75 so that, when detector 73-1 detects media at a corresponding height in tubing 71, a signal is sent to computer 29 indicating that a desired volume of media (e.g., about 900 ml) is present within chamber 61 and tubing 71. Computer 29 then shuts down the flow of additional media into chamber 61 through tubing 63 (by means of a valve not shown). Detector 73-2, which is vertically positioned higher on bracket 75 than is detector 73-1, detects when the aforementioned volume of media has expanded due to having been pre-heated to a desired temperature, e.g., about 38° C. When detector 73-2 detects media at the appropriate level, it sends a signal to computer 29. Computer 29 then causes a motor 79 to drive a piston 81 upwardly and away from an O-ring 83 located at the entrance of a media egress channel 85 formed in base member 57. With piston 81 spaced apart from O-ring 83, media is then allowed to escape from chamber 61 and is conducted through channel 85 into vessel 23 via a media dispensing tube 87.

As can readily be appreciated, the above-described media dispensing means can be modified to measure varying volumes of media by providing a movable piston within chamber 61 that effectively varies the usable volume of chamber 61.

In another embodiment (not shown), the volumetric measuring mechanism of said media dispensing means comprises, instead of the aforementioned arrangement comprising media tubing 63, tubing 71 and media detectors 73-1 and 73-2, a motor driven carriage that adjustably positions a float and a media delivery tube into a pre-calibrated position allowing for a full range of variable media volumes to be obtained automatically. In use, a pump fills the media chamber through the media delivery tube until the volume of media in the media chamber rises to the point where the float is moved upwardly thereby. The upward movement by said float then triggers a switch that causes the pump to reverse direction for a pre-determined period of time, thereby allowing the media to be drawn from the media chamber through the delivery tube until it is drawn down to the desired level.

Referring back now to FIGS. 1 through 5, apparatus 11 further comprises a basket shaft 91. Basket shaft is vertically aligned with vessel 23 and with opening 49 of stage 35 (when stage 35 is in its rearwardmost position) and has a bottom end in the form of a basket lid 93. Lid 93 is appropriately dimensioned to engage a basket 45 from the top by friction-fit. Near its top end 95, basket shaft 91 is removably attached by walking collars (not shown) to a carriage 97, shaft 91 being mechanically coupled to carriage 97 for vertical movement into and out of vessel 23 but being free to move rotationally relative to carriage 97. Rotation of shaft 91 is provided by a motor 99 controlled by computer 29. Carriage 97 is slidably mounted on a pair of posts 101-1 and 101-2. Vertical movement of carriage 97 along posts 101-1 and 101-2 is achieved by means of a threaded drive shaft 103 mechanically coupled to a motor 105 controlled by computer 29.

Figure 15:
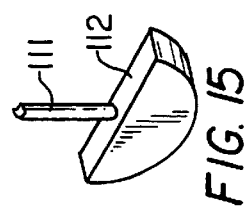
FIG. 15 is a fragmentary perspective view of a paddle shaft which may be used instead of the basket shaft in the apparatus of FIG. 1.

As discussed elsewhere in the present specification, apparatus 11 can be used either for basket-type or paddle-type dissolution of tablets, said paddle-type dissolutions either being of the sinker or sinkerless variety. When apparatus 11 is intended for basket-type dissolution, tablet-containing baskets 45 are loaded into carousel 39 and basket shaft 91 is attached to carriage 97. When apparatus 11 is intended for paddle-type dissolution, tablets (or tablets coupled to sinkers) are placed directly into compartments 43 and basket shaft 91 is replaced with a paddle shaft 111 having a paddle 112 at the bottom end thereof (see FIG. 15).

An opening 113 is provided in platform 21, opening 113 being aligned with basket shaft 91 (or paddle shaft 111) and having a shape appropriate for insertion of basket shaft 91 (or paddle shaft 111) therethrough.

Figure 5:
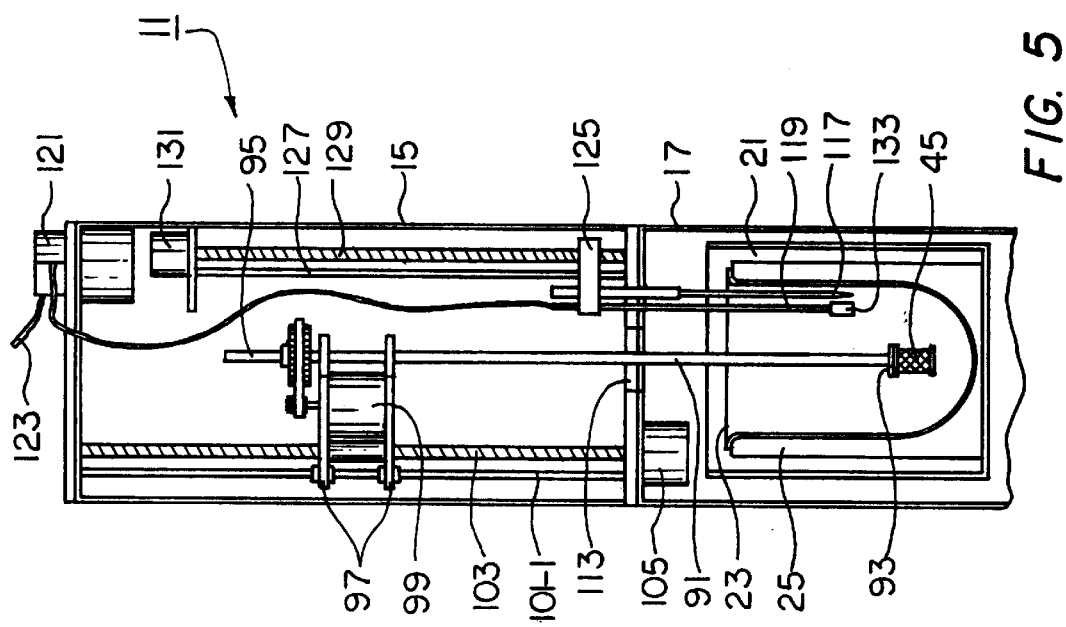
FIG. 5 is a simplified, schematic, fragmentary, front view of the automated tablet dissolution apparatus of FIG. 1, depicting the automated tablet dissolution apparatus during the media sampling stage of its operation, certain aspects of the automated tablet dissolution apparatus not being shown to improve clarity.
Figure 4:
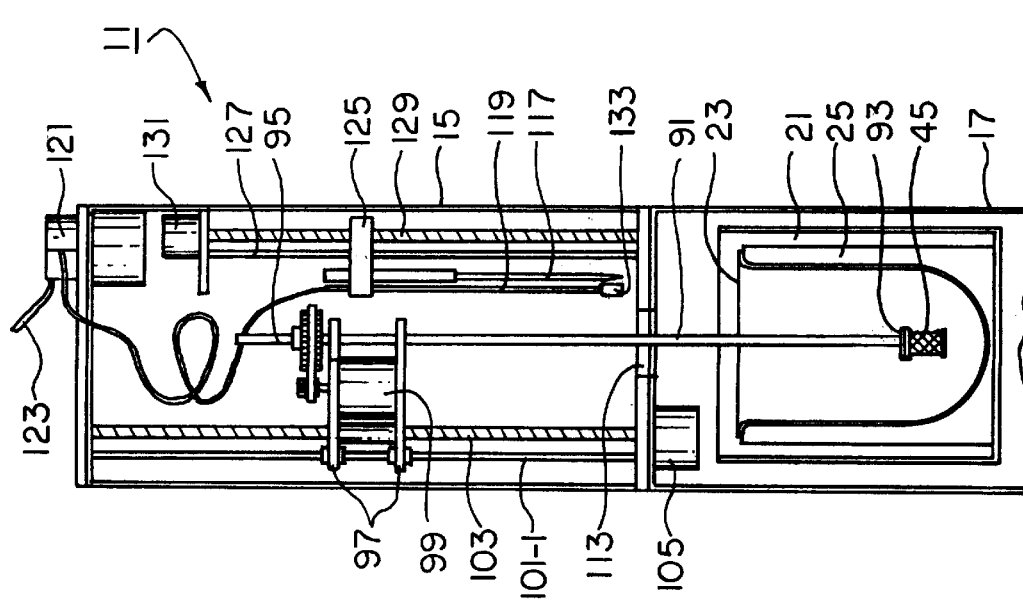
FIG. 4 is a simplified, schematic, fragmentary, front view of the automated tablet dissolution apparatus of FIG. 1, depicting the automated tablet dissolution apparatus during the tablet dissolution stage of its operation, certain aspects of the automated tablet dissolution apparatus not being shown to improve clarity.

Referring now to FIGS. 4 and 5, apparatus 11 further comprises a temperature sensor 117 and a media sampling cannula 119. Sensor 117 is connected to computer 29 so as to provide computer 29 with temperature readings of the dissolution media within vessel 23. Cannula 119 is used to withdraw samples of the media within vessel 23 for external analysis (e.g., chromatography, spectroscopy, etc.) and is connected to a peristaltic pump 121 through a length of flexible tubing 123. Pump 121 is controlled by computer 29. Sensor 117 and cannula 119, both of which are vertically aligned with vessel 23, are fixedly attached near their respective top ends to a carriage 125. Carriage 125, in turn, is slidably mounted on a pair of posts 127. Vertical movement of carriage 125 along posts 127 to permit sensor 117 and cannula 119 to be moved into and out of vessel 23 is achieved by means of a threaded drive shaft 129 mechanically coupled to a motor 131 controlled by computer 29.

As seen in FIGS. 4 and 5, a disposable depth filter 133 is mounted on the bottom end of cannula 119. Filter 133, which may be a conventional depth filter of the type used in tablet dissolution, is used to remove pharmacologically-inactive excipients from the sample collected for analysis using cannula 119. Filter 133 preferably has a pore size of approximately 2 microns.

Referring now to FIGS. 1 through 3 and 16(a) through 16(e), apparatus 11 can be seen to further include means for feeding a filter 133 onto the bottom of cannula 119 and for ejecting from cannula 119 a filter 133 that has been loaded thereonto and no longer needed. In the present embodiment, said feeding and ejecting means comprises a tube 151 into which a plurality of filters 133 have previously been stacked, either manually or otherwise. As seen best in FIGS. 16(a) through 16(e), filters 133 are held in place by an air cylinder 153 (controlled by computer 29) which releasably engages the bottom filter 133 of the stack within tube 151. Said feeding and ejecting means also comprises a carriage assembly 155. Carriage assembly 155 includes a filter receiving member 157. Member 157 is provided with a transverse bore 159 alignable with tube 151 and appropriately dimensioned to receive a filter 133. Member 157 is also provided with a longitudinal slot 161 (see FIG. 19) which extends rearwardly from the front of member 157 into bore 159 and which is appropriately dimensioned, for reasons to become apparent below, to accommodate cannula 119 extending transversely therethrough.

Carriage assembly 155 also includes a base 167, member 157 being mounted on base 167. Base 167 is provided with a transverse bore 168 aligned with bore 159 of member 157 and similarly dimensioned to receive filter 133. As seen best in FIGS. 17(a) and 19, base 167 is also provided with a longitudinal slot 169, which extends rearwardly from the front of base 167 into bore 168 and which is also appropriately dimensioned to accommodate cannula 119 extending transversely therebrough. Carriage assembly 155 also includes a filter stop 171 (shown in isolation in FIGS. 18(a) and 18(b)), which is slidably mounted within longitudinal slot 169 of base 167. Movement of stop 171 within slot 169 is achieved by means of an air cylinder 173, one end of which is inserted into an opening 175 formed in stop 171. Stop 171 is shaped to include a platform 181 which, when positioned between bore 159 of member 157 and bore 168 of base 167, prevents a filter 133 from passing therebetween.

As seen best in FIGS. 1 through 3, 17(a), 17(b) and 19, carriage assembly 155 further includes a block 183 to which base 167 and member 157 are fixedly attached. Block 183, in turn, is slidably mounted on a pair of posts 185. Movement of block 183 along posts 185 is achieved by means a threaded drive shaft 187 mechanically coupled to a motor 188 controlled by computer 29.

Referring back now to FIGS. 16(a) through 16(e), there is illustrated the manner in which the filter feeding and ejecting means ensures that a filter 133 is properly positioned for feeding onto the end of cannula 119. As seen in FIG. 16(a), the temporary retraction of air cylinder 153 allows the bottom filter 133 in tube 151 to drop into bore 159 of member 157. Because stop 171 is positioned so that platform 181 is located between bores 159 and 168, filter 133 is retained within bore 159. In FIG. 16(b), carriage assembly 155 moves laterally in the direction of cannula 119 until bores 159 and 168 are in alignment with a probe 191. Probe 191, which is used to determine whether filter 133 has been loaded into bore 159 correctly (i.e., with its cannula opening 195 facing upwardly) or incorrectly (i.e., with its cannula opening 195 facing downwardly or not loaded at all), is vertically movable by means of an air cylinder 193 controlled by computer 29. Probe 191 is provided with an opening 197, which is detected by an optic sensor 199 if probe 191 extends downwardly to an appropriate depth (see FIG. 16(c)). If, however, as is the case shown in FIG. 16(b), filter 133 is positioned upside down in bore 159, probe 191 will not be able to extend down far enough for sensor 199 to detect hole 197. In such a case, as seen in FIG. 16(d), filter stop 171 will then be retracted and filter 133 will be ejected through bores 159 and 168 into a filter refuse receptacle (not shown). As seen in FIG. 16(e), if no filter has been loaded into bore 159, probe 191 will pass through an opening 200 (see FIG. 18(a)) in filter stop 171 and will move downwardly too far for hole 197 to be detected by sensor 199.

Assuming that filter 133 is properly positioned within bore 159, filter 133 is fed onto cannula 119 as follows: Carriage assembly 155 moves laterally from the aforementioned testing area to a point where cannula hole 195 of filter 133 is aligned with cannula 119. Cannula 119 moves downwardly through an opening 201 in platform 21 into cannula hole 195 until it frictionally engages filter 133 and then moves upwardly a sufficient distance to remove filter 133 from member 157. Carriage assembly 155 then retracts, leaving filter 133 on the bottom end of cannula 119.

Filter 133 is removed from cannula 119 (e.g., after the media has been sampled) as follows: With cannula 119 and filter 133 remaining lowered beyond the height of carriage assembly 155, carriage assembly 155 is moved back to the aforementioned filter loading position, thereby causing cannula 119 to pass through slots 161 and 169 of member 157 and base 167, respectively, until it extends through bores 159 and 168. Cannula 119 is then raised, causing filter 133 to be drawn upwardly through bore 168. As filter 133 moves upwardly through bore 168, however, it becomes wedged in bore 168 against a flange 204 of filter stop 171 and cannot continue upwardly any further. Upward movement of cannula 119, however, is unimpeded; consequently, cannula 119 slips out of filter 133 and is retracted to its initial position. Carriage assembly 155 then moves back over to the filter testing area. Probe 191 then moves downwardly, pushing filter 133 down through bore 168 where it is discarded into the filter refuse receptacle (not shown).

Referring now to FIGS. 17(a), 17(b) and 19, base member 167 can also be seen to be shaped to include an arcuate groove 205 adapted to receive a bottom lip 206 of basket 45. Consequently, basket 45 can be detached from shaft 91 by moving base member 167 relative to basket 45 until lip 206 is inserted into groove 205 and then pulling shaft 91 upwardly until lid 93 disengages from basket 45. Carriage assembly 155, with basket 45 in tow, is then moved laterally to the filter testing position, where an ejector rod 207 pushes basket 45 out of groove 205 into a basket receptacle (not shown).

Figure 20:
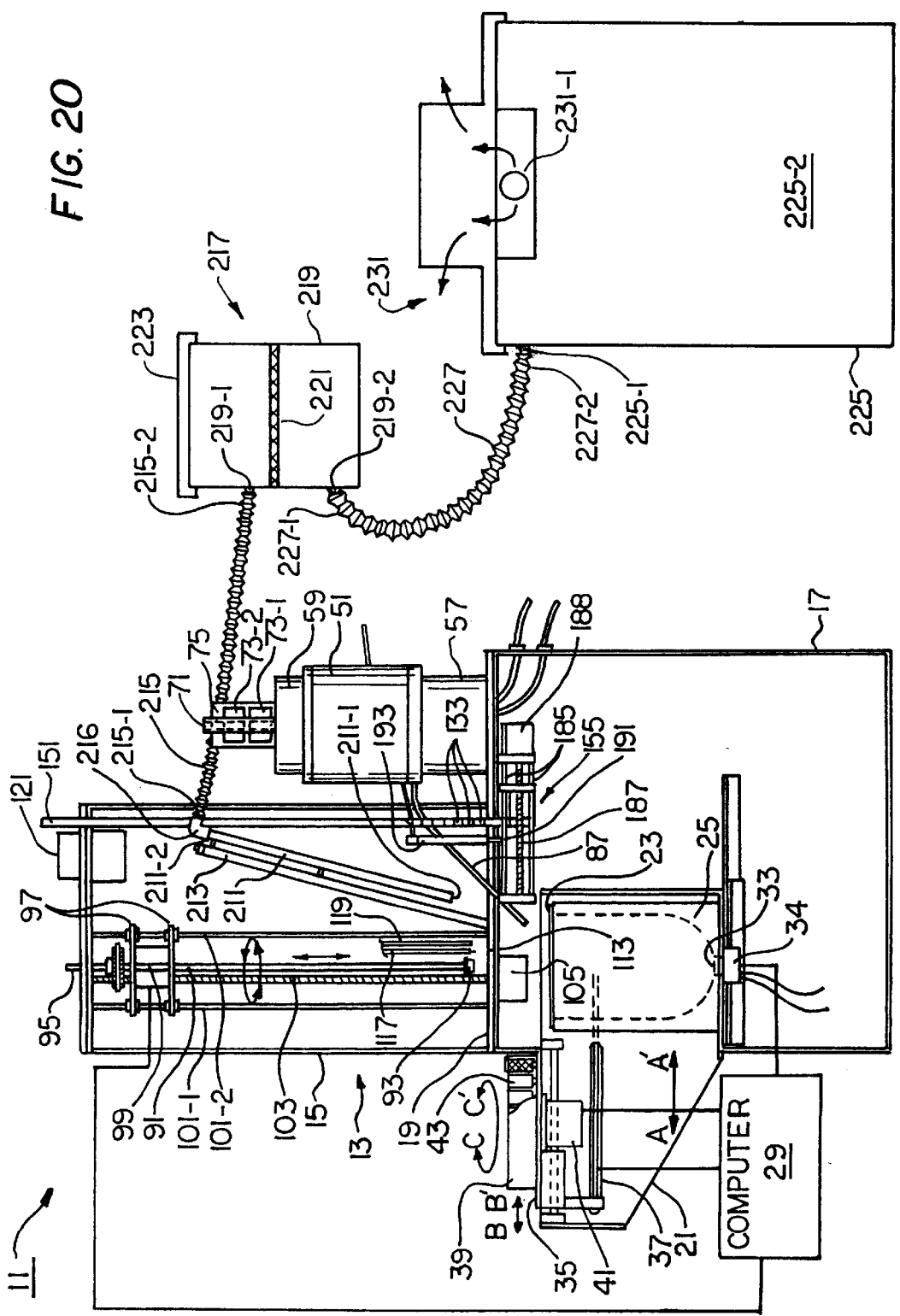
FIG. 20 is a simplified, partly schematic, fragmentary, side elevation view, broken away in part, of the automated tablet dissolution apparatus of FIG. 1, depicting additional details of the automated vessel emptying means of the present invention, certain aspects of the automated tablet dissolution apparatus not being shown to improve clarity.

As seen best in FIG. 20, apparatus 11 further comprises automated means for emptying the contents of vessel 23. In the present embodiment, said automated vessel emptying means comprises a first length of tubing or tube 211. Tube 211, which is preferably made of a rigid material, has a first end 211-1 and a second end 211-2. Tube 211 is mechanically coupled to an air cylinder 213, which in turn is controlled by computer 29. Air cylinder 213 serves to move first end 211-1 of tube 211 into and out of vessel 23, before and after, respectively, the contents of vessel 23 are emptied. As can readily be appreciated, a variety of mechanical means other than an air cylinder can be used to move first end 211-1 of tube 211 into and out of vessel 23.

Said automated vessel emptying means also comprises a second length of tubing or tube 215. Tube 215, which is preferably made of a flexible material, has a first end 215-1 and a second end 215-2. First end 215-1 of tube 215 is connected to second end 211-2 of tube 211, for example, by an elbow-shaped piece of tubing 216.

Said automated vessel emptying means additionally comprises a sinker strainer 217. Although sinker strainer 217 may take many forms, sinker strainer 217 comprises, in the present embodiment, a glass beaker or jar 219, jar 219 having an inlet opening 219-1 and an outlet opening 219-2, inlet opening 219-1 and outlet opening 219-2 being positioned along the side of jar 219, with inlet opening 219-1 being positioned above outlet opening 219-2. Second end 215-2 of tube 215 is coupled to inlet opening 219-1 of jar 219. (As can readily be appreciated, one or more lengths of tubing may be interposed between tube 215 and jar 219, depending on the length of tube 215 and the placement of jar 219.) A screen 221 having a hole size small enough to retain a sinker while still passing waste media therethrough is mounted in jar 219 between openings 219-1 and 219-2. In this manner, media entering jar 219 through inlet opening 219-1 is permitted to pass through screen 221 to outlet opening 219-2 whereas a sinker entering jar 219 through inlet opening 219-1 is not permitted to pass through screen 221. A cover 223 is removably mounted over the open top of glass jar 219 to prevent spillage of media from jar 219 while still enabling an operator to gain access to a sinker seated on screen 221 in order to effect its removal therefrom.

Said automated vessel emptying means further comprises a waste media receptacle 225. Receptacle 225, which has an open top, is provided with an inlet opening 225-1 near said open top and is shaped to define a media chamber 225-2 large enough to hold the waste media from a plurality of tablet dissolution tests. A third length of tubing or tube 227, which is preferably made of a flexible material, has a first end 227-1 and a second end 227-2, first end 227-1 being coupled to outlet opening 219-2 of jar 219, second end 227-2 being coupled to inlet opening 225-1 of receptacle 225.

Said automated vessel emptying means still further comprises a vacuum motor assembly 231 removably mounted in the open top of receptacle 225. Vacuum motor assembly 231 comprises a vacuum motor 231-1 (controlled by computer 29) capable of creating a sufficiently powerful vacuum force (e.g., approximately 80–100 CFM) to remove the entire contents of vessel 23 through tubing 211 in a matter of a few seconds. In this manner, the waste media present in vessel 23 is withdrawn therefrom and is conducted through tubing 211, through tubing 215, through strainer 217, through tubing 227 and into media chamber 225-2 of receptacle 225 whereas a sinker (if any) located in vessel 23 is drawn by said vacuum force from vessel 23 through tubing 211, through tubing 215 and onto screen 221 of strainer 217.

Assembly 231 can be removed from the top of receptacle 225 to enable the contents of media chamber 225-2 to be emptied manually. Alternatively, although not shown, said automated vessel emptying means may further include a float-based or other mechanism for sensing when the level of waste media present within chamber 225-2 has reached a predetermined threshold level and, additionally, automated means for emptying chamber 225-2 when said threshold level has been reached.

Preferably, tubes 211, 215, 216 and 227 (as well as the respective openings of jar 219 and receptacle 225 coupled thereto) have an inner diameter of at least 1¼ inch in order to pass most, if not all, conventional sinkers.

As can readily be appreciated, receptacle 225 could be modified to include a plurality of inlet openings 225-1 so that it could be shared by a plurality of tablet dissolution apparatuses.

As can also readily be appreciated, the particular embodiment of the automated vessel emptying means shown in FIG. 20 could also be modified by positioning a sinker strainer of some form in waste media receptacle 225 after inlet opening 225-1, instead of between tubes 215 and 227, thereby eliminating the need for third piece of tubing 227 (as receptacle 225 could be coupled directly to second end 215-2 of tubing 215). Such a sinker strainer could, for example, take the form of a screen positioned after inlet opening 225-1 and mounted in a drawer or the like that could be pulled out of waste media receptacle 225 in order to facilitate removal of a sinker retained therein.

Although not shown, apparatus 11 also comprises means, controlled by computer 29, for dispensing a washing solution into vessel 23. Washing solution may also be emptied from vessel 23 using the aforementioned vessel emptying means.

To use apparatus 11 for basket-type dissolution, a user places one or more baskets 45 into compartments 43 of carousel 39 and places a tablet inside each basket 45. The user also mounts basket shaft 91 on carriage 97. In addition, the user inputs information into computer 29 regarding several dissolution testing parameters, such as the number of tablets to be tested, whether the dissolution is a basket-type dissolution or a paddle-type dissolution, the time duration of each dissolution, the number of samples to be drawn from each dissolution, the times at which said samples are to be taken, the temperature at which dissolution is to be performed, etc. The dissolution testing parameters may be either the same or different for multiple tablets tested sequentially.

From this point onward, no more human intervention is necessary as apparatus 11 automatically performs the following steps, among others: The media dispensing means volumetrically measures the desired quantity of media, pre-heats and sparges said quantity of media and then dispenses the pre-heated and sparged quantity of media into vessel 23. The media within vessel 23 is then maintained at the appropriate dissolution temperature by platen 25. Carousel 39 is positioned so that a compartment 43 holding a tablet-containing basket 45 is situated directly under shaft 91. Shaft 91 is then lowered until lid 93 engages basket 45. Shaft 91 is then raised, thereby removing basket 45 from carousel 39. Carousel 39 is then moved to its forwardmost position, and shaft 91 is lowered until basket 45 is positioned approximately 1 inch from the bottom of vessel 23. Basket 45 is then rotated at approximately 50–150 rpm for the dissolution period specified (see FIG. 2). A filter 133 is fitted onto cannula 119 and, at the time specified, a sample is withdrawn from vessel 23. Where multiple samples are taken during the dissolution period, either the same filter 133 or different filters 133 may be used. After use, the filter 133 is removed from cannula 119 and discarded. At the conclusion of the dissolution period, rotation of basket 45 is halted and shaft 91 is raised until lip 206 of basket 45 is vertically aligned with groove 205 of base member 167. Base member 167 is then moved laterally towards basket 45 until lip 206 is inserted into groove 205. Shaft 91 is then raised, thereby detaching shaft 91 from basket 45. Base member 167 then moves back laterally, causing ejector rod 207 to eject basket 45 from base member 167 into a used basket receptacle. At the same time that basket 45 is being detached from shaft 91, tube 211 is lowered into vessel 23 and the contents of vessel 23 are removed in the manner described above. While this is being done, a washing solution is dispensed into vessel 23, tube 211 similarly being used to remove the washing solution from vessel 23. Lid 93 of shaft 91 may be lowered into vessel 23 to also be washed by the washing solution. At the conclusion of the above-described procedure, shaft 91 and carriage assembly 155 are returned to their initial positions. Where a second dissolution is to be performed, carousel 39 is then positioned so that a second basket 45 is aligned with shaft 91 and the foregoing procedure is repeated.

To use apparatus 11 for paddle-type dissolution, the above-described procedure is performed with the following exceptions: Instead of attaching shaft 91 to carriage 97, the user attaches paddle shaft 111 to carriage 97. Moreover, instead of placing tablets inside baskets 45 that are, in turn, inserted into carousel 39, the user places a tablet or a combination of a tablet and a sinker directly into each compartment 43 of carousel 39. The tablets or tablet/sinker combinations are then dispensed from carousel 39 into vessel 29 in the manner shown in FIG. 12. Because the same paddle 112 and paddle shaft 111 are used for each dissolution, the basket-basket shaft detachment procedure described above is not applicable.

As can readily be appreciated, two or more independently operable apparatuses 11 can be hooked up to same computer 29.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A tablet dissolution apparatus comprising:
   (a) a dissolution vessel;
   (b) means for agitating the contents of said dissolution vessel; and
   (c) a dissolution vessel emptying mechanism, said dissolution vessel emptying mechanism comprising
      (i) a waste media receptacle, said waste media receptacle having an inlet opening and defining a media chamber,
      (ii) tubing means having a first end insertable into the dissolution vessel and a second end attached to said inlet opening of said waste media receptacle, and
      (iii) automated vacuum means for emptying the contents of said dissolution vessel into said tubing means and for conducting any media in said tubing means to said media chamber of said waste media receptacle.

2. The tablet dissolution apparatus as claimed in claim 1 further comprising automated means for volumetrically-obtaining, heating and sparging a quantity of media and for dispensing said quantity of media into said dissolution vessel.

3. The tablet dissolution apparatus as claimed in claim 1 further comprising automated sampling means for sampling the contents of said dissolution vessel.

4. The tablet dissolution apparatus as claimed in claim 1 further comprising automated means for dispensing a tablet into said dissolution vessel.

5. The tablet dissolution apparatus as claimed in claim 1 further comprising automated means for heating said dissolution vessel.

6. The tablet dissolution apparatus as claimed in claim 1 further comprising means for imaging the contents of said dissolution vessel.

7. The tablet dissolution apparatus as claimed in claim 1 wherein said agitating means is automated.

8. The tablet dissolution apparatus as claimed in claim 1 further comprising automated means for volumetrically-obtaining, heating and sparging a quantity of media and for dispensing said quantity of media into said dissolution vessel, automated sampling means for sampling the contents of said dissolution vessel, automated means for dispensing a tablet into said dissolution vessel, automated means for heating said dissolution vessel, and automated means for imaging the contents of said dissolution vessel.

9. The tablet dissolution apparatus as claimed in claim 8 wherein said agitating means is automated.

10. A tablet dissolution apparatus comprising:
   (a) a dissolution vessel;
   (b) means for agitating the contents of said dissolution vessel; and
   (c) a dissolution vessel emptying mechanism, said dissolution vessel emptying mechanism comprising:
      (i) a waste media receptacle, said waste media receptacle having an inlet opening and defining a media chamber,
      (ii) tubing means having a first end insertable into the dissolution vessel and a second end attached to said inlet opening of said waste media receptacle,
      (iii) automated means for moving said first end of said tubing means into and out of, respectively, the dissolution vessel,
      (iv) automated vacuum means for creating a vacuum drawing from within said waste media receptacle to said first end of said tubing means, said vacuum being sufficiently strong to empty the contents of said dissolution vessel, and
      (v) a sinker strainer disposed between said first end of said tubing means and said media chamber.

11. The tablet dissolution apparatus as claimed in claim 10 wherein said tubing means comprises a first tube, said first tube having a first end and a second end, said first end of said first tube being insertable into said dissolution vessel, a second tube, said second tube having a first end and a second end, said first end of said second tube being connected to said second end of said first tube, said second end of said second tube being connected to said sinker strainer, and a third tube, said third tube having a first end and a second end, said first end of said third tube being connected to said sinker strainer, said second end of said third tube being connected to said inlet opening of said waste media receptacle.

12. The tablet dissolution apparatus as claimed in claim 11 wherein said sinker strainer comprises a beaker, said beaker having an inlet opening, an outlet opening, and a screen, said screen being disposed between said inlet opening and said outlet opening, said screen being constructed to pass media therethrough and not to pass a sinker therethrough.

13. A tablet dissolution apparatus comprising:
   (a) a dissolution vessel;
   (b) means for agitating the contents of said dissolution vessel; and
   (c) a dissolution vessel emptying mechanism, said dissolution vessel emptying mechanism comprising:
      (i) a waste media receptacle, said waste media receptacle having an inlet opening and defining a media chamber,
      (ii) a first tube, said first tube having a first end and a second end, said first end being insertable into said dissolution vessel,
      (iii) a second tube, said second tube having a first end and a second end, said first end of said second tube being connected to said second end of said first tube,
      (iv) straining means disposed between said dissolution vessel and said waste media receptacle for straining a sinker from the fluid contents of a dissolution vessel, said straining means having an inlet opening and an outlet opening, said second end of said second tube being connected to said inlet opening of said straining means,
      (v) a third tube, said third tube having a first end and a second end, said first end of said third tube being connected to said outlet opening of said straining means, said second end of said third tube being connected to said inlet opening of said waste media receptacle,
      (vi) automated vacuum means for creating a vacuum drawing from within said waste media receptacle to said first end of said first tube, said vacuum being sufficiently strong to empty the contents of said dissolution vessel.

14. The tablet dissolution apparatus as claimed in claim 13 wherein said dissolution emptying mechanism further comprises automated means for moving said first end of said first tube into and out of, respectively, said dissolution vessel.

* * * * *